(12) United States Patent
Lehmann et al.

(10) Patent No.: US 10,918,769 B2
(45) Date of Patent: Feb. 16, 2021

(54) MEDICAL DRAINAGE DEVICE WITH SQUEEGEE-BASED LUMEN CLEANER AND METHOD OF DRAINING A BIOLOGICAL FLUID FROM THE BODY OF A PATIENT

(71) Applicant: Boehringer Technologies, LP, Phoenixville, PA (US)

(72) Inventors: Allison Lloyd Lehmann, Norristown, PA (US); Christopher L. Radl, Malvern, PA (US)

(73) Assignee: Boehringer Technologie, LP, Phoenixville, PA (US)

( * ) Notice: Subject to any disclaimer, the term of this patent is extended or adjusted under 35 U.S.C. 154(b) by 563 days.

(21) Appl. No.: 15/936,975

(22) Filed: Mar. 27, 2018

(65) Prior Publication Data
US 2018/0280593 A1    Oct. 4, 2018

Related U.S. Application Data

(60) Provisional application No. 62/480,821, filed on Apr. 3, 2017.

(51) Int. Cl.
*A61M 1/00* (2006.01)

(52) U.S. Cl.
CPC .......... *A61M 1/0078* (2013.01); *A61M 1/008* (2013.01); *A61M 1/0033* (2014.02); *A61M 1/0039* (2013.01); *A61M 2205/0216* (2013.01)

(58) Field of Classification Search
CPC .............. A61M 1/0078; A61M 1/0033; A61M 1/0039; A61M 1/008; A61M 2205/0216

USPC ........................................................ 604/319
See application file for complete search history.

(56) References Cited

U.S. PATENT DOCUMENTS

| 4,596,554 | A | * | 6/1986 | Dastgeer | A61B 90/00 604/101.05 |
|---|---|---|---|---|---|
| 4,893,634 | A | * | 1/1990 | Kulik | A61B 1/015 600/561 |
| 5,141,503 | A | * | 8/1992 | Sewell, Jr. | A61M 1/0011 604/317 |
| 5,197,963 | A | * | 3/1993 | Parins | A61B 18/1482 606/41 |
| 6,984,226 | B1 | * | 1/2006 | Abell | A61M 3/0208 604/514 |
| 7,854,728 | B2 | | 12/2010 | Boyle, Jr. | |
| 7,951,243 | B2 | | 4/2011 | Boyle, Jr. et al. | |
| 8,048,233 | B2 | | 11/2011 | Boyle, Jr. et al. | |

(Continued)

*Primary Examiner* — Andrew J Mensh
(74) *Attorney, Agent, or Firm* — Ceasar Rivise, PC

(57) ABSTRACT

A drainage device and method of draining a biological fluid from the body of a patient is disclosed. The drainage device includes a drainage tube, a pressure relief assembly, a cleaner assembly, and a housing. The drainage tube includes an array of apertures in it through which biological fluid from the patient can flow for collection by a collection canister. The cleaner assembly includes a squeegee unit configured to be pulled in a proximal direction from a distally located position in the drainage tube to scrape any biological material adhering on the inner surface of the drainage tube and carry it to the collection canister. The pressure relief assembly serves to equalize the pressure in the drainage tube as it is being cleaned. The squeegee unit also acts as a pressure relief valve to equalize the pressure within the drainage tube when the squeegee unit is retracted back to its distally located position.

14 Claims, 5 Drawing Sheets

(56) References Cited

U.S. PATENT DOCUMENTS

| | | | |
|---|---|---|---|
| 8,246,752 B2 * | 8/2012 | Boyle, Jr. | B08B 9/0436 |
| | | | 134/8 |
| 8,388,759 B2 | 3/2013 | Boyle, Jr. et al. | |
| 8,702,662 B2 | 4/2014 | Boyle | |
| 8,951,355 B2 | 2/2015 | Boyle, Jr. et al. | |
| 9,180,233 B2 * | 11/2015 | Kagan | A61M 1/0088 |
| 2006/0264988 A1 * | 11/2006 | Boyle | A61M 1/0039 |
| | | | 606/159 |
| 2012/0289892 A1 * | 11/2012 | Shtul | A61M 3/0216 |
| | | | 604/28 |
| 2014/0150782 A1 * | 6/2014 | Vazales | A61B 1/126 |
| | | | 128/202.16 |
| 2015/0231361 A1 * | 8/2015 | O'Keefe | A61M 25/00 |
| | | | 604/500 |

* cited by examiner

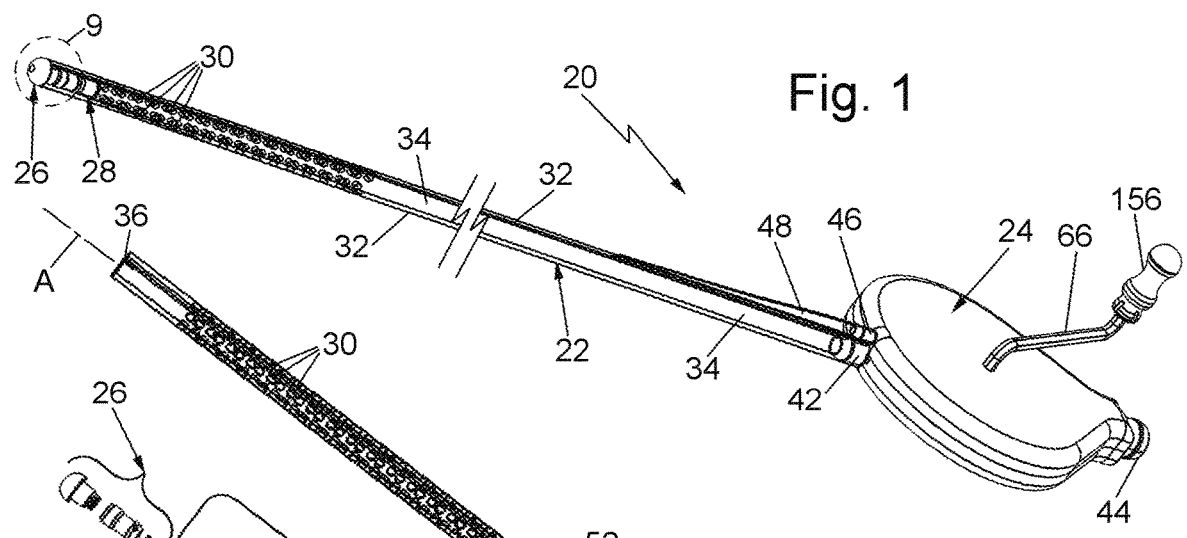
Fig. 1
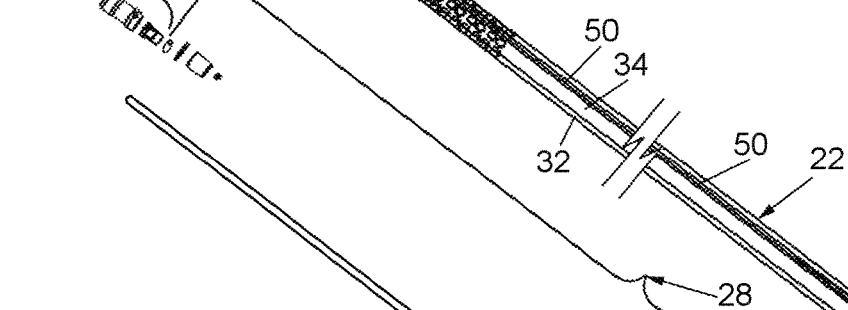
Fig. 2
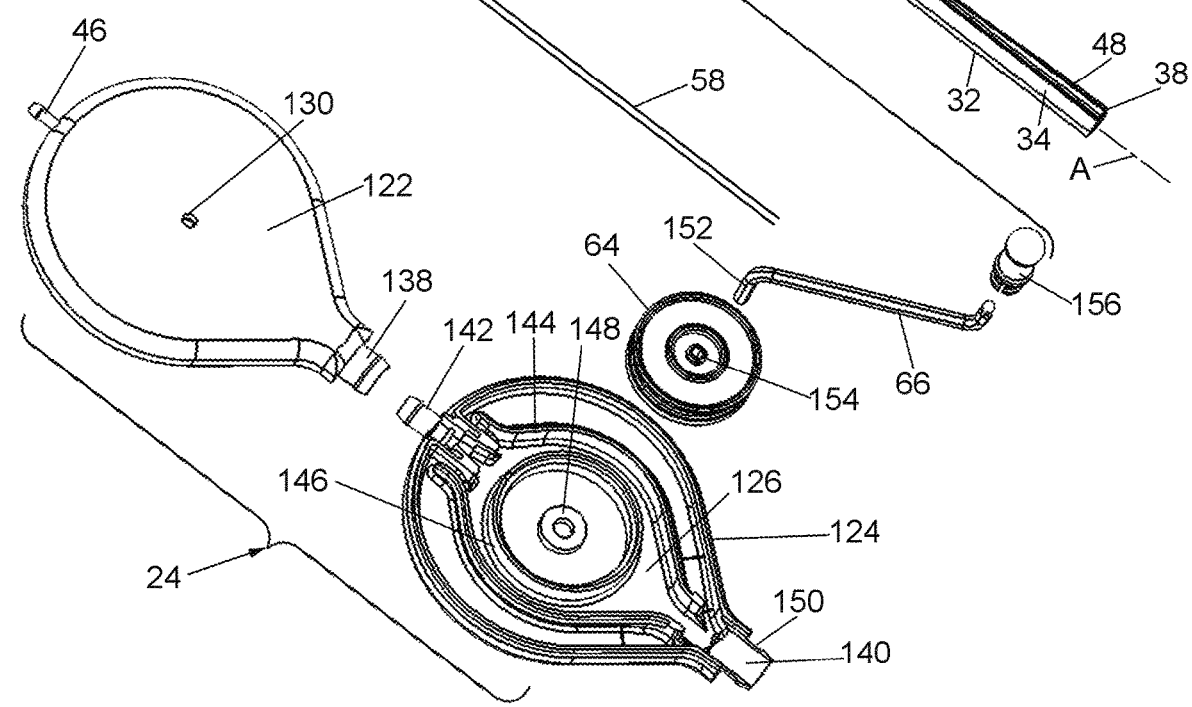

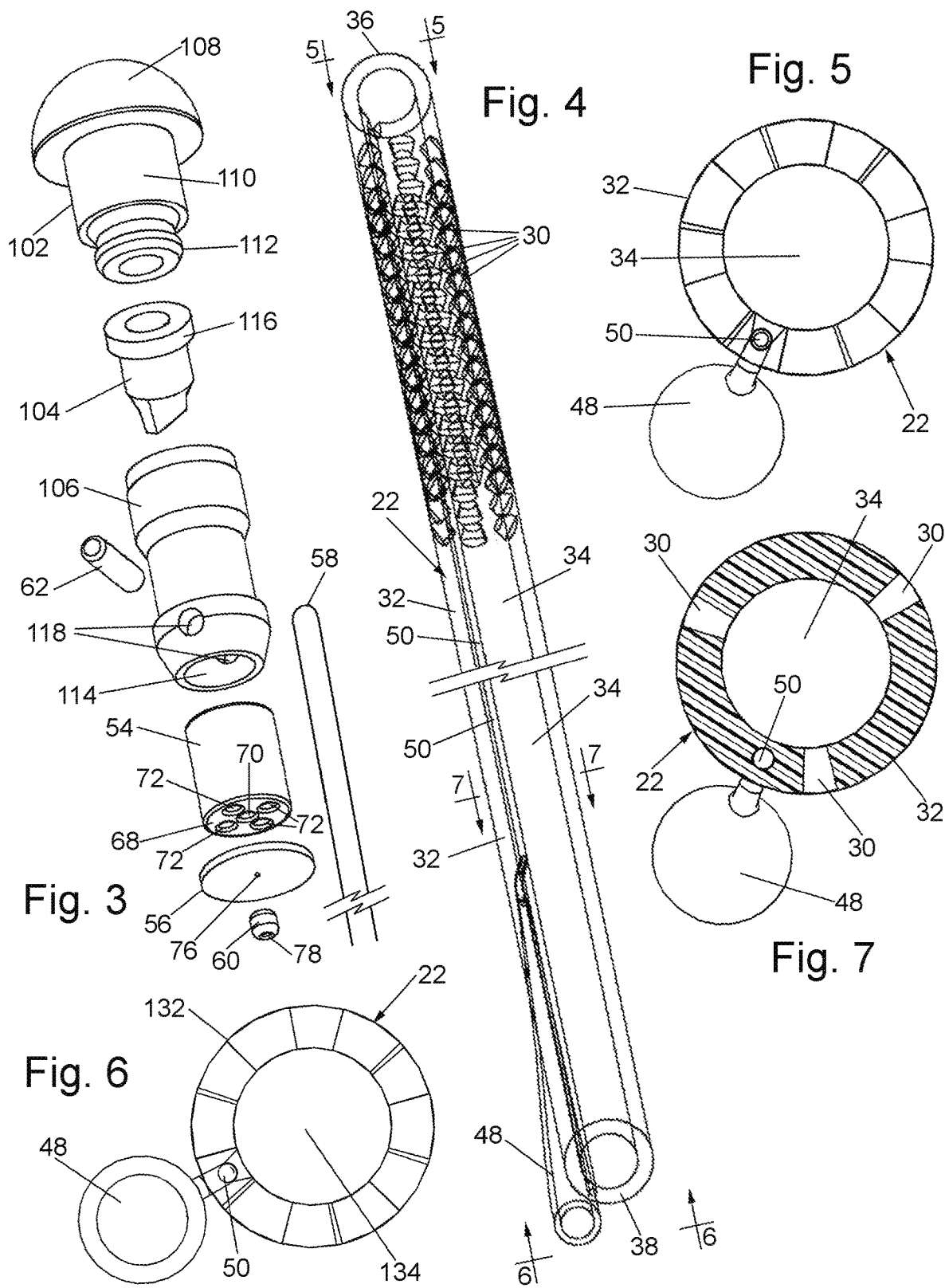

MEDICAL DRAINAGE DEVICE WITH SQUEEGEE-BASED LUMEN CLEANER AND METHOD OF DRAINING A BIOLOGICAL FLUID FROM THE BODY OF A PATIENT

CROSS-REFERENCE TO RELATED APPLICATIONS

This utility application claims the benefit under 35 U.S.C. § 119(e) of Provisional Application Ser. No. 62/480,821 filed on Apr. 3, 2017 entitled Medical Drainage Device with Squeegee-Based Lumen Cleaner and Method of Draining a Biological Fluid From the Body of a Patient. The entire disclosure of this provisional application is incorporated by reference herein.

FIELD OF THE INVENTION

The disclosed invention relates to medical devices and more particularly to medical, e.g., chest, drainage tubes which include squeegee means for removing any biological materials from the interior of the tubes to prevent clogging thereof and methods of draining biological fluids from the body of a patient.

BACKGROUND OF THE INVENTION

Following cardiothoracic surgeries, or after suffering chest trauma, drainage tubes are placed within the chest to evacuate fluids such as blood, air, serosal fluid, etc. Most of these fluids drain successfully. However, blood frequently clots, clogging up the chest drainage tubes as well as the chest space. This places stress on the heart and lungs and can lead to life threatening situations. Maintaining chest tube patency ensures a clear path to drain blood and other fluids from the chest.

Currently chest drain tube clogs are most commonly cleared by milking/stripping of the tube from the outside, which causes high negative pressure forces to be placed on the organs and tissues of the chest. This may result in damage to these organs and tissues. Other methods of clearing clogs in chest drain tubes involve disconnecting the chest drain tube from the rest of the drainage system, in order to stick another long tube or other object into the chest drain to scrape or spray or suction loose the clog. This compromises the sterile field, putting the patient at higher risk of infection, and requires skilled personnel such as a surgeon, to carry out the procedure.

In U.S. Pat. No. 7,854,728 (Boyle Jr); U.S. Pat. No. 8,702,662 (Boyle Jr); U.S. Pat. No. 8,246,752 (Boyle Jr.); U.S. Pat. No. 7,951,243 (Boyle Jr. et al.); U.S. Pat. No. 8,048,233 (Boyle Jr. et al.); U.S. Pat. No. 8,388,759 (Boyle Jr. et al.); and U.S. Pat. No. 8,951,355 (Boyle Jr. et al.) there are disclosed various devices for cleaning chest drainage tubes without compromising sterility. While those devices may be generally suitable for their intended purposes they nevertheless leave much to be desired from various standpoints, e.g., restricted usage to chest tubes which are maintained in a straight orientation, with nothing that can pinch or restrict the inside diameter of the tube, limiting placement to anterior areas of the pericardium only. Furthermore, the internal scraping features of the devices of those patents may not totally clear the tube of clotted blood.

Accordingly, a need exists for device which overcomes the drawbacks of the prior art. The subject invention addresses that need by providing a drainage tube which includes an internal cleaning assembly including a squeegee unit for cleaning the lumen in the drainage tube.

SUMMARY OF THE INVENTION

One aspect of this invention is a drainage device for draining a biological fluid, e.g., blood, components of blood, and other fluids, from the body of a patient. The drainage device comprises a drainage tube having a sidewall with a drainage lumen extending therethrough. The drainage lumen has an inner surface. The sidewall includes distal end, a distal end portion located adjacent the distal end and proximally thereof, a proximal end portion, and a longitudinal axis extending the length of the sidewall. The proximal end portion is configured for location outside the body of the patient for coupling to a fluid collection canister. The distal end portion of the drainage tube is configured to be introduced into the body of the patient and includes an array of plural apertures in communication with the drainage lumen and configured for receipt of the biological fluid from the body of the patient. A pressure relief lumen extends along the sidewall from a point at the proximal end portion to a pressure relief port located distally of the array of apertures. A pressure relief assembly including a one-way pressure relief valve in communication with the pressure relief port is located within the drainage lumen distally of the array of apertures. A lumen cleaner assembly including a squeegee unit is located in the drainage lumen proximally of the one-way pressure relief assembly and distally of the array of apertures. The squeegee unit is moveable relative to the drainage lumen by a filament located within the drainage lumen, whereupon pulling of a portion of the filament causes the squeegee unit to move in the proximal direction down the drainage lumen to scrape any biological material off the inner surface of the drainage lumen and to carry any biological material scraped off of the inner surface of the drainage lumen to a passageway coupled to the fluid collection canister for collecting the biological material.

In accordance with one preferred aspect of the drainage device of this invention, the one-way pressure relief valve is configured to open during the movement of the squeegee unit in the proximal direction in the event that pressure within the drainage tube distally of the squeegee unit exceeds a predetermined value, whereupon air or fluid is enabled to flow from the pressure relief lumen into and through the one-way pressure relief valve into the drainage lumen distally of the squeegee unit.

In accordance with another preferred aspect of the drainage device of this invention, the squeegee unit is configured to be moved in a distal direction through the drainage lumen by pulling on a portion of the filament.

In accordance with another preferred aspect of the drainage device of this invention, the squeegee unit is configured to act as a pressure relief valve when it is moved in the distal direction through the drainage lumen, whereupon air or fluid may flow around the squeegee unit from a proximal side of the squeegee unit to a distal side of the squeegee unit.

In accordance with another preferred aspect of the drainage device of this invention, the squeegee unit comprises an elastomeric disc having a small central portion fixedly secured to a distally located backing body. The backing body is configured to hold the elastomeric disk in a generally planar state when the squeegee unit is moved in the proximal direction and enable the elastomeric disk to bend or bow into a generally cup-shaped member when the squeegee unit is moved in the distal direction.

In accordance with another preferred aspect of the drainage device of this invention, the backing body comprises a cylindrical or semi-spherical piston having plural longitudinal passageways extending therethrough and a generally planar proximal surface abutting the elastomeric disk.

In accordance with another preferred aspect of the drainage device of this invention, the drainage device additionally comprises a housing having a hollow interior, a first port in fluid communication with the hollow interior, a second port in fluid communication with the hollow interior, and a third port in fluid communication with the hollow interior.

In accordance with another preferred aspect of the drainage device of this invention, the first port is configured to be connected to the proximal end portion of the drainage tube, and wherein the second port is configured to be connected to a conduit coupled to the fluid collecting canister.

In accordance with another preferred aspect of the drainage device of this invention, the lumen cleaner assembly comprises a pulley located in the distal end portion of the sidewall and about which the filament extends, and wherein one portion of the filament is fixedly secured to the squeegee unit.

In accordance with another preferred aspect of the drainage device of this invention, the lumen cleaner assembly additionally comprises a rotatable spool located in the housing. The spool is configured to have portions of the filament wrapped around the spool. The spool is rotatable in one direction to cause the filament to move the squeegee unit through the drainage lumen in a distal direction and also rotatable in a second direction, opposite to the first direction, to cause the filament to move the squeegee unit through the drainage lumen in the proximal direction.

Another aspect of this invention is a method of draining a biological fluid, e.g., blood, components of blood, and other fluids, from the body of a patient. The method comprises providing a drainage device comprising a drainage tube having a sidewall with a drainage lumen extending therethrough. The drainage lumen has an inner surface. The sidewall includes a distal end, a distal end portion located adjacent the distal end and proximally thereof, a proximal end portion, and a longitudinal axis extending the length of the sidewall. The proximal end portion is configured for location outside the body of the patient for coupling to a fluid collection canister located outside the body of the patient. The distal end portion of the drainage tube includes an array of plural apertures in the sidewall in communication with the drainage lumen and configured for receipt of the biological fluid from the body of the patient. A pressure relief lumen extends along the sidewall from a point at the proximal end portion to a pressure relief port located distally of the array of apertures. A pressure relief assembly including a one-way pressure relief valve in communication with the pressure relief port is located within the drainage lumen distally of the array of apertures. A lumen cleaner assembly including a squeegee unit is located in the drainage lumen proximally of the one-way pressure relief assembly and distally of the array of plural apertures. The squeegee unit is moveable relative to the drainage lumen by a filament located within the drainage passageway. The distal end portion of the drainage tube is introduced into the body of the patient, whereupon biological fluid from the body of the patient flows into the plural apertures and from there through the drainage tube for collection in the fluid collecting canister. Biological material adhering to the inner surface of the drainage lumen is scraped off of the inner surface of the drainage lumen by pulling a portion of the filament to cause the squeegee unit to move in a proximal direction down the drainage lumen to scrape such biological material off the inner surface of the drainage lumen and to carry any such biological material scraped off of the inner surface of the lumen to a passageway coupled to the fluid collection canister for collecting the biological material.

In accordance with another preferred aspect of the method of this invention, the one-way pressure relief valve is configured to open during the movement of the squeegee unit in the proximal direction in the event that pressure within the drainage tube distally of the squeegee unit exceeds a predetermined value, whereupon air or fluid is enabled to flow from the pressure relief lumen into and through the one-way pressure relief valve into the drainage lumen distally of the squeegee unit.

In accordance with another preferred aspect of the method of this invention, the method additionally comprises pulling a portion of the filament to cause the squeegee unit to move in a distal direction through the drainage lumen, whereupon the squeegee unit is brought back to a position distally of the array of apertures.

In accordance with another preferred aspect of the method of this invention, the squeegee unit is configured to act as a pressure relief valve when it is moved in the distal direction through the drainage lumen, whereupon air or fluid may flow around the squeegee unit from a proximal side of the squeegee unit to a distal side of the squeegee unit.

BRIEF DESCRIPTION OF THE DRAWING FIGURES

FIG. 1 is an isometric view of one exemplary medical drainage device constructed in accordance with this invention;

FIG. 2 is an exploded isometric view of the various components making up the exemplary drainage device of FIG. 1;

FIG. 3 is an enlarged exploded isometric view of a one-way pressure relief valve assembly and a portion of a lumen cleaning assembly of the exemplary drainage device of FIG. 1;

FIG. 4 is an enlarged isometric view of a drainage tube of the exemplary drainage device of FIG. 1;

FIG. 5 is an enlarged distal end view of the drainage tube taken along line 5-5 of FIG. 4;

FIG. 6 is an enlarged proximal end view of the drainage tube taken along line 6-6 of FIG. 4;

FIG. 7 is an enlarged cross-sectional view of the drainage tube taken along line 7-7 of FIG. 4;

DETAILED DESCRIPTION OF THE PREFERRED EMBODIMENTS

Figure 8:
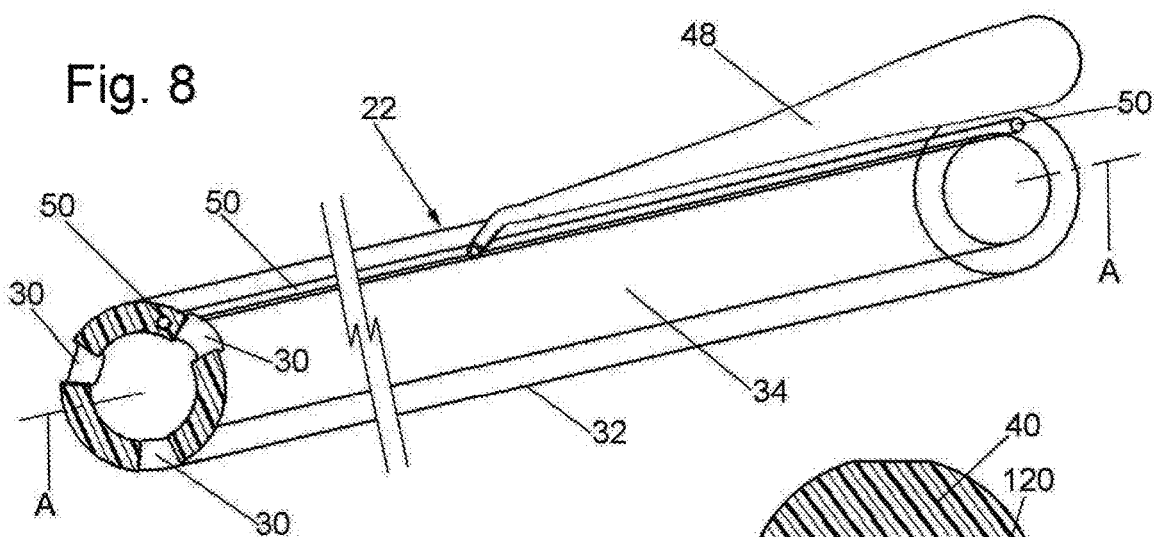
FIG. 8 is an enlarged isometric view, partially in section, of the proximal end portion of the drainage tube shown in FIG. 4.

Referring now to the drawings wherein like characters refer to like parts there is shown in FIG. 1 one exemplary embodiment of a medical drainage device 20 constructed in accordance with this invention. The device 20 is formed of biocompatible materials and basically comprises an elongated flexible drainage tube 22, an adaptive connector case or housing 24, a pressure relief assembly 26 and a lumen cleaner assembly 28. The particular exemplary embodiment of the drainage tube 22 as shown in FIG. 1 is in the form of a chest drainage tube having plural inlet apertures 30 (to be described later) that are located adjacent the distal end of the drainage tube.

The proximal end of the drainage tube is connected to the adaptive case or housing 24 by a coupling, which shall be described later. The interior of the case or housing 24 is hollow and in fluid communication with the coupling to which the drainage tube is connected. The case or housing 24 also includes another coupling, that shall also be described later, and which is configured to be connected to a conduit or tube (not shown) forming a component of a conventional suction-assisted drainage canister system (also not shown). Such systems typically include a suction-operated fluid collection canister, a pressure regulator and a canister connection tube through which the fluid being drained from the patient is carried into the interior of the fluid collection canister. In addition, the case or housing 24 includes another coupling, that shall also be described later, and which is connected to a pressure relief lumen (also to be described later) extending along the drainage tube to the pressure relief assembly.

As best seen in FIGS. 1, 2, 4 and 8 the drainage tube 22 is an elongated flexible member having a circular sidewall 32. The sidewall bounds a circular drainage lumen 34 extending from its distal end 36 to its proximal end 38. The drainage lumen is centered along the central longitudinal axis A of the drainage tube 22. Since the exemplary drainage tube 22 is configured for use as a chest drainage tube, the inner diameter of the lumen 34 is approximately 6 mm, while the outer diameter of the sidewall 32 is approximately 9 mm, as is conventional. However, these dimensions are merely exemplary. As such, the central lumen 34 can be of any suitable internal diameter and the outer diameter of the sidewall can be of any suitable outer diameter. For example, for applications draining fluid from a lung, where there is likely to be less blood, the drainage tube 22 can have a smaller inside diameter and a smaller outside diameter. In any case, the material making up the drainage tube is selected to be any suitable flexible material, like those transparent material tubes used in conventional medical drainage tubes, but which is nevertheless fairly stiff to prevent the tube from collapsing or kinking during use.

Figure 9:
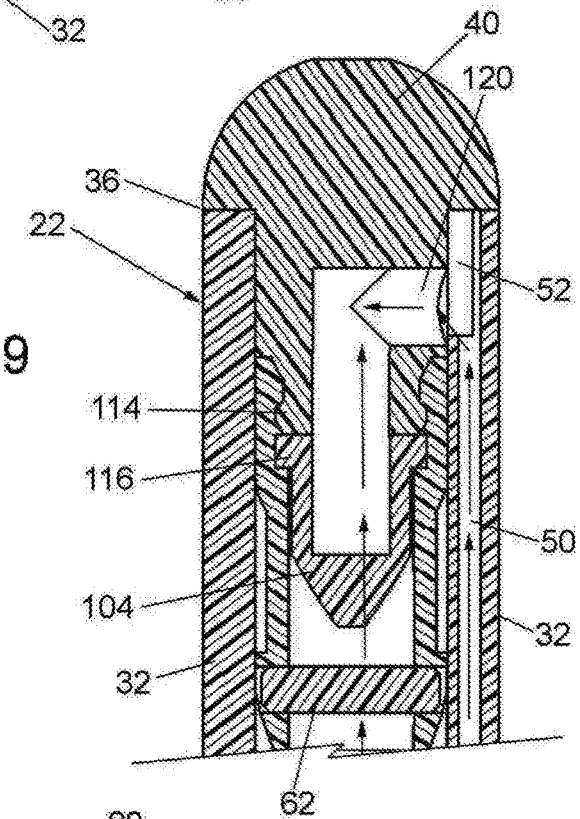
FIG. 9 is an enlarged longitudinal sectional view of the distal end of the drainage device shown within the broken line circle designated by the reference number 9 in FIG. 1.

As best seen in FIGS. 1 and 9 the distal end of the drainage device 20 is in the form of a rounded or curved, e.g., hemispherical, cap sealing the distal end 36 of the drainage tube's sidewall 34. That cap will be described in detail later and constitutes a portion of the pressure relief assembly 26. The proximal end 38 of the sidewall of the drainage tube is configured to be connected to a first coupling 42 forming an inlet port of the case or housing 24. The case or housing 24 will be described in detail later. Suffice it for now to state that it is formed of two shell sections that are fixedly secured together to form a hollow interior chamber therebetween. The inlet port 42 is in fluid communication with the hollow interior chamber. The case includes a second coupling 44 forming an outlet port of the case and which is also in fluid communication with the hollow interior chamber. The outlet port coupling 44 is configured to be connected to the distal end of a collection canister tube (not shown). The proximal end of the collection canister tube is connected to a conventional suction-operated fluid collection canister. The case also includes a third coupling 46 forming an air equalizing outlet port of the case. The pressure equalizing outlet port 46 is in communication with the interior chamber of the case and is configured to be coupled to the proximal end of a pressure equalizing tube 48 is coupled to the drainage tube 22. The pressure equalizing tube 48 is coupled to an pressure equalizing lumen 50 (FIGS. 1, 4, 8 and 9) which extends longitudinally within the sidewall 32 from the proximal end 38 to the distal end 36. The pressure equalizing lumen 50 terminates at a port 52 (FIG. 9) extending radially inward to the drainage lumen 34 at the distal end 36 of the drainage tube. The pressure equalizing lumen 50 serves to provide equalizing air to the pressure relief assembly 26 during the cleaning of the drainage lumen by the lumen cleanser assembly 28, as will be described later.

As mentioned above, and as best seen in FIGS. 1 and 4-7 a portion of the sidewall of the drainage tube 22 adjacent the distal end 36 includes a multitude of small inlet holes or apertures 30. These apertures extend through the sidewall 32 from the outer surface of the sidewall to the drainage lumen 34. The apertures 30 are arranged in an array extending about the periphery of the sidewall. For the exemplary chest drainage tube shown in FIG. 1 the array of apertures 30 extends for approximately six inches from a point close to the distal end of the drainage tube and for each given length of sidewall there are three apertures, of approximately 3 mm internal diameter, equidistantly spaced about the periphery of the sidewall. However, that arrangement is merely exemplary of various arrangements for the array of apertures, their number, size and location. In any case, the apertures 30 are configured to enable biological fluids to be drained from the patient and collected in the externally located fluid collection canister. In particular, when the drainage device 20 is in place, with the drainage tube 22 within the portion of the patient's body to be drained of a biological fluid, suction is applied from the fluid collection canister through the path consisting of the collection canister tube, the hollow interior chamber of the case 24, and the drainage lumen 34 of the drainage tube to the apertures 30. The suction applied at those apertures, which is approximately forty cm of water, draws the biological fluid from the patient's body into those apertures and back through the foregoing path for collection in the collection canister.

The use of an array of very small apertures about the periphery of the distal end portion of the drainage tube 22 minimizes and possibly eliminates any tissue intrusion, or tissue damage. In particular, the use of smaller holes or apertures through which suction is applied to drain the biological fluids increases the amount of pressure required to cause the same degree of damage to delicate tissue, e.g., lung tissue, than may be created by larger suction holes under a much lower pressure. Therefore, smaller apertures may be used safely in combination with higher than currently acceptable pressures with less risk of injury to the patient.

Figure 10:
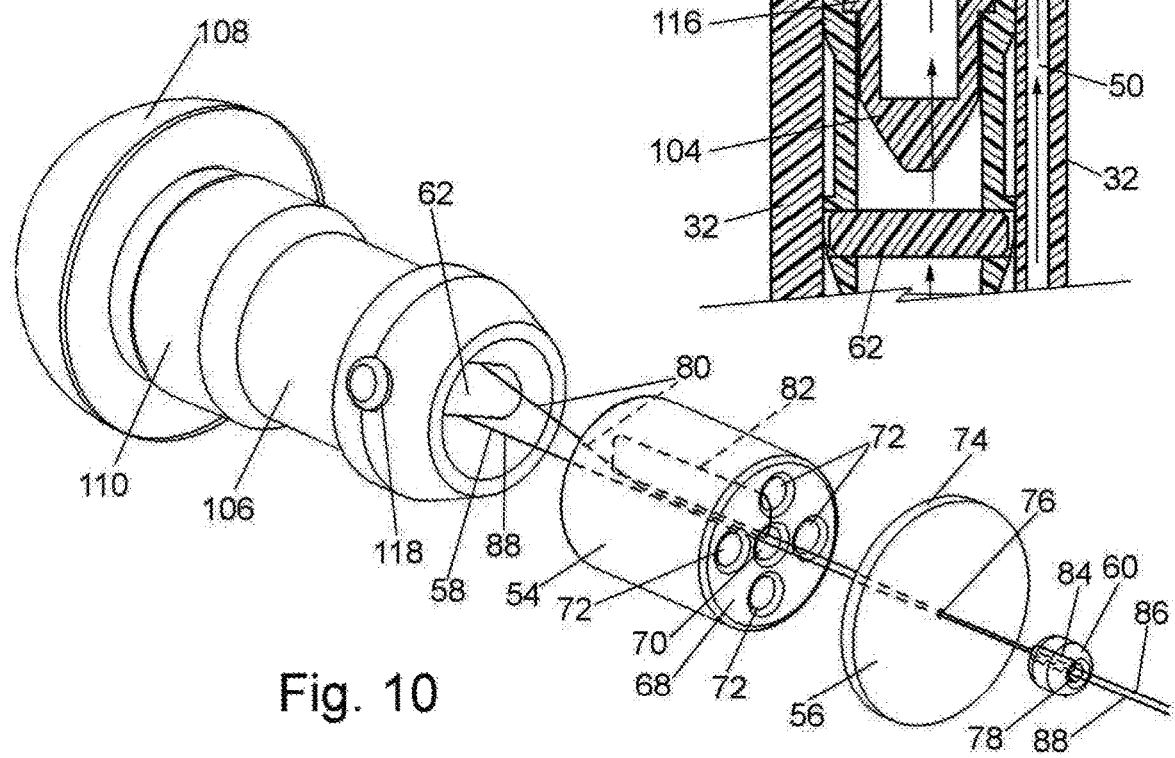
FIG. 10 is an enlarged exploded isometric view of the one-way pressure relief valve assembly and a portion of the lumen cleaning assembly showing their interconnection.
Figure 11:
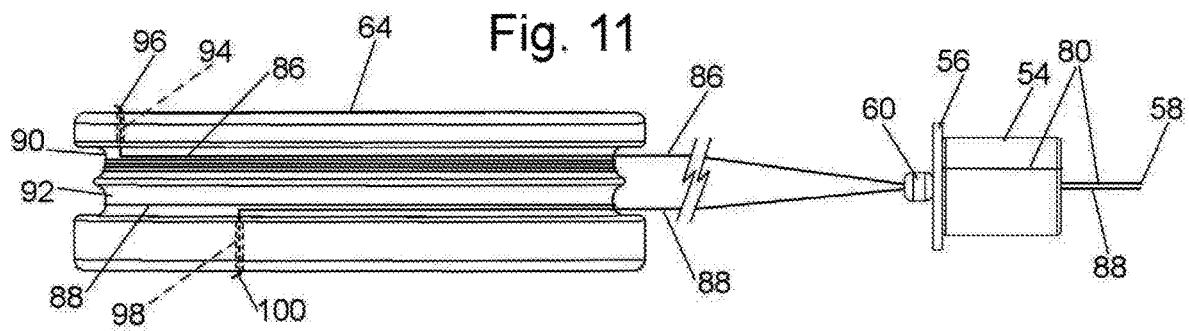
FIG. 11 is an enlarged side elevation view of a portion of the lumen cleaning assembly.
Figure 12:
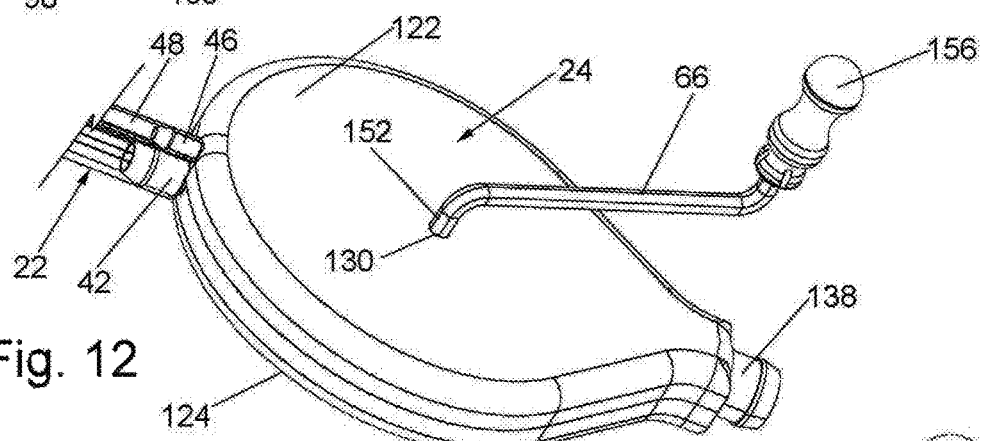
FIG. 12 is an enlarged isometric view of the case or housing and portions of the drainage tube of the exemplary medical drainage device of FIG. 1.
Figure 13:
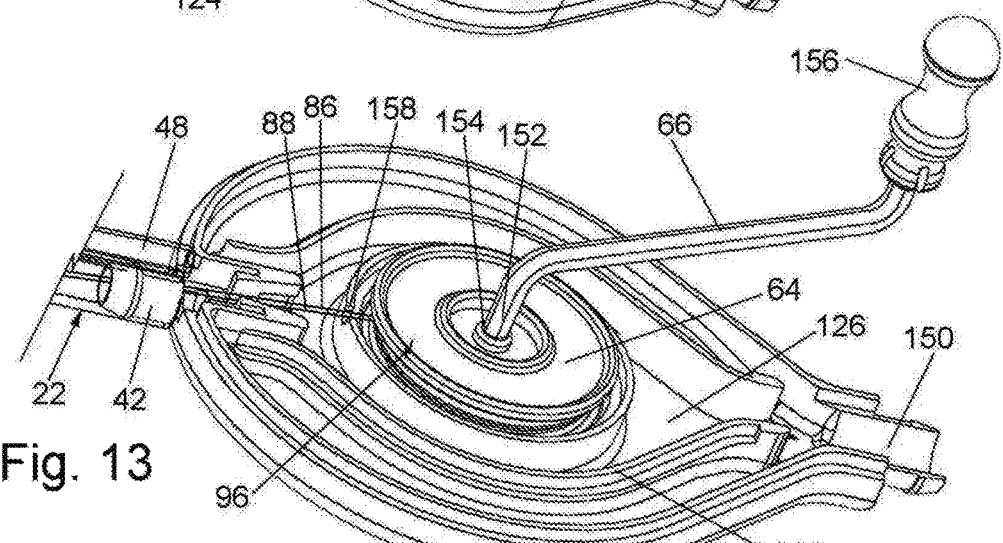
FIG. 13 is a slightly more enlarged isometric view of the portion of the drainage device shown in FIG. 1, but with one shell portion of the case or housing removed to show the internal components located within the case or housing.
Figure 14:
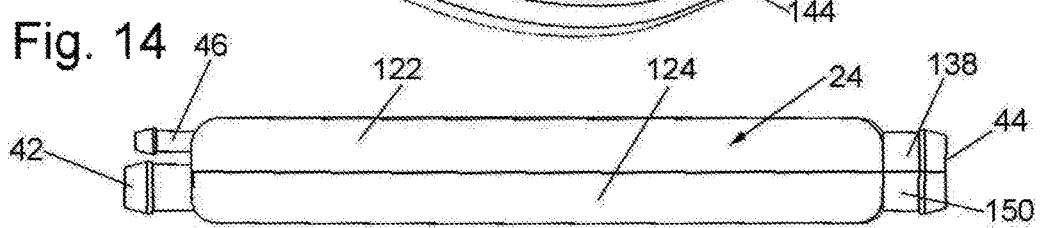
FIG. 14 is a side elevation view of the case or housing of the drainage device of FIG. 1.

In order to prevent blood, blood clots, or any other biological material, fluid or debris entering into the drainage tube 22 from sticking or accumulating on the inner surface of its drainage lumen 34 to the extent that such accumulation would either clog that lumen or restrict that lumen in a manner detrimental to the patient, the drainage device 20 includes the heretofore identified lumen cleaner assembly 28. That assembly is best seen in FIGS. 3, 10 and 11 and basically comprises a backing body or piston 54, an elastomeric squeegee disk 56, a flexible elongated string, cable or filament 58, a locking bead 60, a pulley 62, a spool 64, and a rotatable crank 66 (FIGS. 1 and 13). The details of the construction, interconnection and operation of those components will be described shortly. Suffice it for now to state that the backing body or piston 54, the squeegee disk 56 and the bead 60 are connected together to form a "squeegee unit" that is configured to be drawn down the length of the drainage tube tube's central lumen from a point just distally of the array of aperture to the proximal end of the of the central lumen by the filament 58. In particular, respective portions of the filament 58 are wound about respective annular grooves (to be described later) extending about the periphery of the spool 64. Thus, rotation of the spool in one rotational direction by operation of the crank 66 causes on portion of the filament to be wound about one of the annular grooves in the spool to thereby pull on the contiguous portions of the filament in the proximal direction, whereupon another portion of the filament, which extends about the pulley 62, and is fixedly secured to the squeegee unit pulls that unit distally until it is in what can be called its normal or resting position. In that position it is located distally of the array of apertures and proximally of the pressure relief assembly 26.

As will be described in detail later, when the squeegee unit is in its normal or resting position the drainage device is ready for use to drain biological fluids from the patient. To that end the distal end portion of the drainage tube is inserted into the patient's body and the location to be drained, e.g., the patient's chest. The suction-operated canister can then be operated to produce controlled suction in the drainage tube. That action will result in the biological fluid of the patient flowing into the array of apertures 30 and down the drainage tube, whereupon that fluid will be collected in the fluid collection canister.

When it is desired to clean the inner surface of the drainage lumen of any biological material which had adhered to that surface all that is required is to rotate the crank 66 in the opposite rotational direction, whereupon the concomitant rotation of the spool 64 in that opposite rotational direction causes another portion of the filament to be wound about the other of the annular grooves in the spool 64 to thereby pull on another portion of the filament to which the squeegee unit is fixedly secured. That action moves the squeegee unit in the proximal direction, whereupon the peripheral edge of the squeegee disk 56 closely engages and scrapes along the inner surface of the drainage lumen to act as a squeegee and thereby push any biological material which had adhered to the inner surface to the inlet port 42 and from there it flows through the housing or casing 24 to the collection canister. As will also be described later the squeegee unit is configured so that it also serves as a one-way valve when that unit is moved in the proximal-to-distal travel direction to bring the squeegee unit back to its normal or resting position located distally of the array of apertures.

As mentioned earlier the components making up the squeegee unit are the backing body or piston 54, the elastomeric squeegee disk 56, and the locking bead 60, all of which are fixedly secured together by portions of the filament 58. In one exemplary embodiment the backing body or piston 54 is a short cylindrical member whose outer diameter is slightly less than the inner diameter of the drainage lumen 34 to enable it to freely move through the drainage lumen irrespective of bends in the drainage tube. The proximal end surface 68 of the piston is planar and extends perpendicularly to the central longitudinal axis A. The piston includes a central passageway 70 extending through it from the proximal end surface to the distal end surface and is centered on the longitudinal axis A. Four other passageways 72 extend through the piston from the proximal end surface to the distal end surface and are equidistantly spaced about the longitudinal axis A. The squeegee disk 56 is a generally planar elastomeric member of circular profile and whose outer diameter is slightly larger than the inside diameter of the drainage lumen so that the periphery 74 of the disk will tightly engage the inner surface of the drainage lumen. In accordance with one preferred embodiment of this invention the disk is formed of a fabric-reinforced rubber. The disk includes a very small pin-prick aperture 76 in its center. The planar distal surface of the disk 56 abuts the planar proximal surface 68 of the piston 54. The locking bead 60 is a small diameter member having a central passageway 78 extending longitudinally through it and centered on the longitudinal axis. The bead 60 is disposed proximally of the proximal surface of the disk and in abutment therewith, such that the disk is tightly sandwiched and secured between the bead and the piston.

The securement of the piston 54, the squeegee disk 56 and the locking bead 60 is achieved by portions of the filament 58. In particular, as best seen in FIG. 10 one portion 80 of the filament 58 extends from the pulley 62 into the distal end of the central passageway 70 from whence it exits the proximal end of that passageway and enters the proximal end of an adjacent passageway 72. It then extends down that passageway 72 and exits the distal end of that passageway from whence it re-enters distal end of the central passageway 70 and passes through the central passageway to exit the proximal end of the central passageway. Thus, the portion 80 of the filament forms a loop 82 in the passageways 70 and 72. The portion 80 of the filament then passes through the pin-prick aperture 76 in the squeegee disk and from there it passes into the distal end of the central passageway 78 in the locking bead 60. The portion 80 of the filament passes through the central passageway 78 and exits the proximal end thereof and then extends backward in the distal direction over a portion of the outer surface of the bead, whereupon it re-enters the central passageway 78 to exit that passageway at the proximal end thereof. Thus, the exiting portion 80 of the filament forms a loop 84 about the central passageway and outer surface of the bead 60. The filament portion 80 is pulled tight so that the loops 80 and 82 tightly hold the piston and the locking bead with the squeegee disk tightly sandwiched therebetween. The portion of the filament exiting the proximal end of the bead 60 is designated by the reference number 86 and extends through the drainage lumen to the interior of the case or housing 24 where it is wound about one of the annular grooves in the periphery of the spool 64. The other portion of the filament 58 which is located on the opposite side of the pulley 62 from the filament portion 80 is designated by the reference number 88. The filament portion 88 extends into the distal end of the central passageway 70 of the piston and through that passageway, then through the pin-prick aperture 76 in the disk, and then through the central passageway 78 in the locking bead. The portion 88 of the filament exiting the locking bead at the proximal end thereof extends through the drainage lumen to the interior of the case or housing 24 where it is wound about the other of the annular grooves in the periphery of the spool 64.

Turning now to FIG. 10 it can be seen that the spool is a circular member having two annular recesses or grooves 90 and 92 extending about the periphery of the spool. The filament portion 86 is wound about the annular groove 90, with the end of that filament portion 86 being fixedly secured to the spool. In particular, the end of the filament portion 86 extends through a small passageway 94 in a flange of the spool to the outer surface of the spool where it is formed into a knot 96 holding it in place. In a similar manner the filament portion 88 is wound about the annular groove 92, with the end of that filament portion 88 being fixedly secured to the spool. In particular, the end of the filament portion 88 extends through a small passageway 98 in the other flange of the spool to the outer surface of the spool where it is formed into a knot 100 holding it in place.

It should be noted that while the embodiment of the spool and filament as just described has the two ends of the filament 58 fixedly secured to the spool 62 that is not mandatory. For example, since the filament will be used to pull the squeegee unit up and down the drainage lumen, that filament may not be secured directly to the spool. By not securing the filament ends to the spool, the spool may serve as a clutch mechanism, allowing the filament to slip if too much force is applied, which action might minimize patient risk in the event of tissue intrusion into the drainage tube.

Turning now to FIGS. 3 and 9, the details of the pressure relief assembly 26 will now be described. That assembly comprises a mushroom shaped cap member 102, a one-way check valve 104, and a tubular body member 106. Those components are fixedly secured, e.g., snap-fit, together to form an integral unit or assembly. The mushroom shaped cap member 102 includes a semi-spherical head 108 from which a cylindrical sidewall 110 projects downward. The interior of the sidewall is in the form of a hollow chamber. The proximal end 112 of the sidewall 110 is in the form of an annular ridge configured to snap-fit into a matingly shaped recess 114 (FIG. 9) in the central passageway of the tubular body member 106. The one-way, check valve 104 is an elastomeric duck-bill valve (but could be any other type of one-way, check valve) and is located within the central passageway 114. In particular, the duck-bill check valve 104 includes an annular flange 116 which is disposed on an annular ledge 116 in the central passageway of the tubular body member 106, with that flange being tightly interposed between the proximal end 112 of the cap member and the ledge 116. The proximal end of the tubular body member includes a pair of holes 118 that are aligned with each other and which extend perpendicular to the longitudinal axis A. Those holes serve to mount the pulley 62, which in this embodiment is merely in the form of a pin about which the filament 58 extends. A radially extending hole or port 120 (FIG. 9) is located in the sidewall 110 and is in fluid communication with the hollow chamber bounded by the sidewall.

The integral unit forming the pressure relief assembly 26 is fixedly secured at the distal end 36 of the drainage tube. In particular, the undersurface of the head 108 abuts the distal end 36 of the drainage tube 22, with the cylindrical sidewall extending into the drainage passageway 34. Thus the hemi-spherical head of the cap member 102 forms the distal end of the drainage device 20.

As mentioned earlier, the cleaner assembly 28 is normally in what can be called its resting position located distally of the array of apertures 30, like shown in FIG. 1. In this position the assembly 28 is ready to clean (e.g., scrape) any biological material which had adhered to the inner surface of the drainage lumen 34. When such action is required the crank 66 is rotated in a rotational direction to cause the filament portion 86 to be wound up in the annular channel 90 of the spool 64, whereupon the remaining portion 86 of the filament is pulled in the proximal direction. Since that filament portion is fixedly secured to the squeegee unit of the cleaner assembly 28 by virtue of the loops 80 and 82, the squeegee unit is pulled in the proximal direction through the drainage lumen. The fact that the outer diameter of the backing member or piston 54 is just slightly less than the inner diameter of the drainage lumen 34 coupled with the fact that the proximal end surface 68 of the piston is planar keeps the squeegee disk 56 flat. Accordingly, upon the sliding motion of the squeegee unit in the proximal direction through the drainage lumen the periphery of the squeegee disk 56 tightly engages the inner surface of the drainage lumen as it moves therealong. This squeegee/scraping action increases the pressure distally (behind) of the squeegee disk. That increased pressure could present a danger to the patient if not for operation of the pressure relief assembly 26. In particular, the increased pressure distally of the squeegee disk appears on the outer surface of the duck-bill check valve 104. Once that externally applied pressure reaches the cracking pressure of the duck bill check valve, e.g., 50 cm of water, it opens, whereupon air or fluid can flow into the drainage lumen distally of the squeegee disk to equalize the pressure thereat. Accordingly, sterile air or fluid from within the case or housing 24 and which is isolated from the ambient air outside of the drainage device 20, can flow through the port 46 and the associated pressure equalizing tube 48, into the pressure equalizing lumen 50. From there the sterile air or fluid can flow to the port 52 in communication with the port 120 in the cap 102, and from there into and out of the duck bill valve as shown by the arrows in FIG. 9. That air or fluid flow equalizes the pressure in the drainage lumen distally of the squeegee disk to the pressure in that lumen proximally of the squeegee disk, which proximal pressure is the safe pressure established by a pressure regulator forming a portion of the conventional suction-operated collection canister system.

The manner of connection of the squeegee disk 56 to the piston 54 creates what can be considered to be a pressure equalizing one-way valve which operates during the retraction or distal movement of the squeegee unit back to its resting position. In this regard, since the squeegee disk 56 is an elastomeric member which is only secured to the flat proximal end 68 of the piston 54 at the center of the piston by the small locking bead 60 the distal movement of the squeegee unit will have the effect of bowing or bending the squeegee disk 56 into a somewhat cup-shaped concave member, with the concave side being the distal side of the squeegee disk. This bending of the squeegee disk enables air or fluid to flow around its periphery and around the outer periphery of the piston and through the plural longitudinally extending passageways 70 and 72 in the piston. That air or fluid flow around the squeegee disk from the proximal side to the distal side thereof results in the equalization of pressure within the drainage lumen 34 distally of the squeegee unit during the retraction of the squeegee unit to its resting position since the one way duck bill check valve 104 of the pressure relief assembly 26 will be closed at this time.

Turning now to FIGS. 2 and 12-19 the details of the construction of the adaptive connector case or housing 24 will now be described. That case or housing is called "adaptive" inasmuch as it enables the smaller diameter drainage tube 22 which is connected to the coupling 42 to transition to the large diameter canister connection tube 15 which is connected to the coupling 44. As mentioned earlier the canister connection tube typically comes standard with conventional suction-assisted chest drainage canister systems. As best seen in FIG. 2, the adaptive connector case or housing 24 basically comprises a pair of shell sections 122 and 124 which are fixedly connected together to form a hollow body having a hollow interior chamber 126. The chamber 126 is isolated from the ambient atmosphere when the shell sections are secured together.

Figure 15:
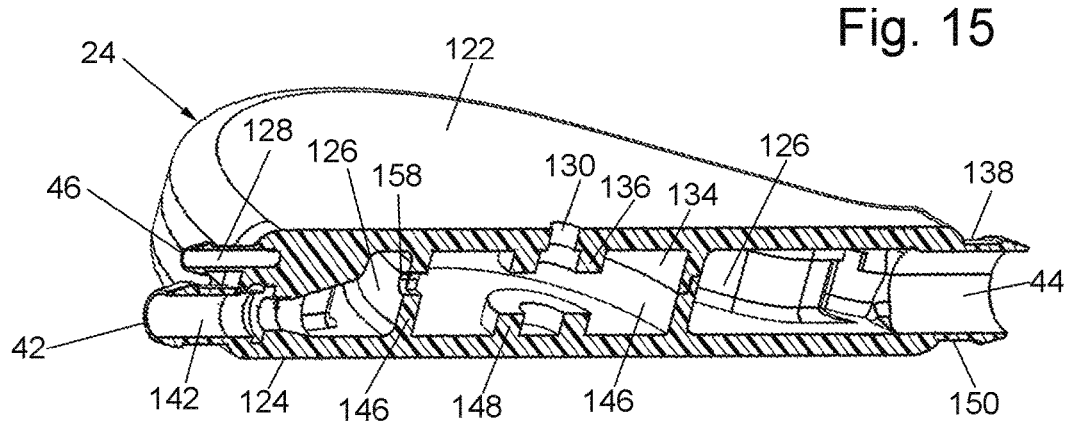
FIG. 15 is an isometric view of the case or housing assembly shown in FIG. 14, but sectioned longitudinally.
Figure 16:
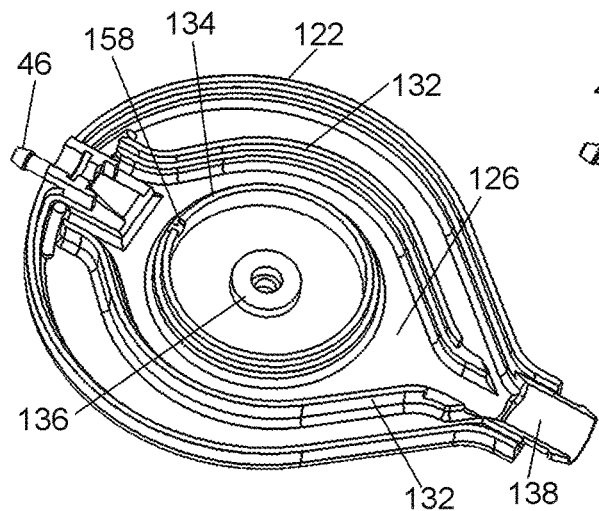
FIG. 16 is an isometric view showing the interior of one shell section making up the case or housing assembly shown in FIGS. 14 and 16.
Figure 17:
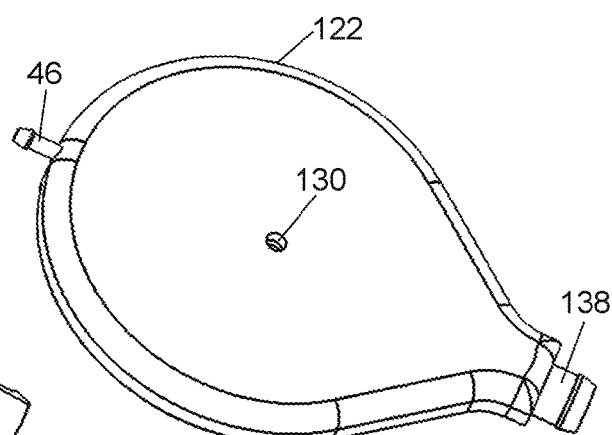
FIG. 17 is an isometric view showing the exterior of the shell section shown in FIG. 16.

The shell section 122, which is best seen in FIGS. 15-17, includes the heretofore identified coupling 46 extending from the front or distal end thereof. The coupling 46 is a tubular member having a central passageway 128 (FIG. 15) which is in fluid communication with the interior chamber 126 of the case or housing. The coupling 46 is configured to be frictionally fit within the hollow passageway of the air equalizing tube 48. The central portion of the shell 122 includes an opening 130 through which a portion of the crank 66 extends. Plural curved walls 132 project inward from the inner surface of the shell section 122. A circular wall 134 also projects inward from the inner surface of the shell section 122. The wall 134 conjoins with a circular wall of the shell section 124 to contain the spool 64 therein. A smaller and lower height circular wall 136 projects inward from the inner surface of the shell section 122 and is centered in the circular wall 134. The smaller circular wall 136 serves as a first hub for the case or housing establishing a rotation axis for the spool 64. Thus, the hub is configured to fit within a corresponding first circular recess in the spool 64 to enable the spool to rotate thereabout. The shell section 122 also includes a semi-circular projection 138 extending from the rear or proximal end thereof. That projection is configured to conjoin with a similarly shaped projection of the shell section 124 to form the heretofore identified outlet coupling 44.

Figure 18:
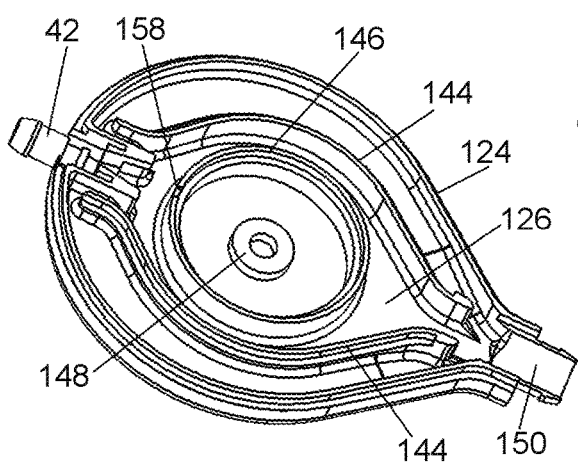
FIG. 18 is an isometric view showing the interior of another shell section making up the case or housing assembly shown in FIGS. 14 and 16.
Figure 19:
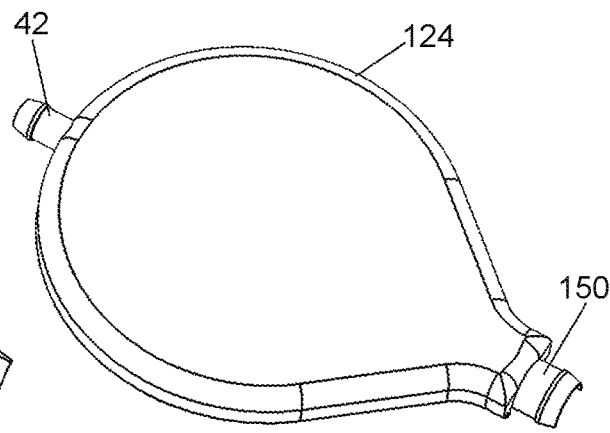
FIG. 19 is an isometric view showing the exterior of the shell section shown in FIG. 18.

The shell section 124 which is best seen in FIGS. 15, 18 and 19 includes the heretofore identified inlet coupling 42 extending from the front or distal end thereof. The coupling 42 is a tubular member having a central passageway 142 (FIG. 15) which is in fluid communication with the interior chamber 126 of the case or housing. The coupling 42 is configured to be frictionally fit within the proximal end of the drainage lumen 34. Plural curved walls 144 project inward from the inner surface of the shell section 124. A circular wall 146 also projects inward from the inner surface of the shell section 124. That wall is the wall that conjoins with the wall 134 of the shell section 122 to contain the spool 64 therein. A smaller and lower height circular wall 148 projects inward from the inner surface of the shell section 124 and is centered in the circular wall 146. The smaller circular wall 148 is axially aligned with the first hub 136 and serves as a second hub which fits within a second corresponding circular recess in the spool to enable the spool to rotate about its rotation axis. The shell section 124 also includes a semi-circular projection 150 extending from the rear or proximal end thereof. The projection 150 is configured to conjoin with the semicircular projection 138 of the shell section 122 to form the heretofore identified outlet coupling 44. The outlet coupling 44 is a tubular member having a central passageway 140 (FIG. 15) which is in fluid communication with the interior chamber 126 and is configured to be frictionally fit within the hollow passageway of the canister connection tube.

As best seen in FIG. 15 the inner edges of the walls 132 and 134 of the shell section 122 abut the inner edges of the walls 144 and 146 of the shell section 124 to form a lap joint when those shell sections are fixedly secured together. Moreover the peripheral edges of the shell sections 122 and 124 abut as clearly shown in FIG. 14.

As mentioned above the spool 64 is located within the conjoining circular walls 134 and 146 and is mounted on the hubs 136 and 148 so that it can rotate thereabout. The rotation of the spool about its rotation axis is accomplished by the crank 66. To that end, the crank 66 is an elongated member having an offset hex-shaped inner end 152 which is configured to fit within a hex-shaped socket 154 (FIG. 13) located on the side of the spool extending into the circular wall 132 of the shell section 122. The opposite end of the crank 66 is also offset and is in the form of a handle. The conjoining circular walls 134 and 146 include a small opening or window 158 (FIGS. 13 and 15) through which the filament portions 86 and 88 extend to be wound on the spool.

It should be pointed out at this juncture that all of the abutting components of the shell sections 122 and 124 are secured to each other in a fluid-tight arrangement. Moreover, the opening 130 through which the inner end 152 of the crank extends is sealed to the ambient atmosphere. Accordingly, when the distal end portion of the drainage device is located within the body of the patient with the drainage tube 22 being connected to the housing via couplings 42 and 46, and the canister connection tube is connected to the housing via coupling 44, the entire interior of the drainage device 20 is isolated from the ambient atmosphere, thus maintaining the sterility within that system. Further still, the conjoining walls within the interior of the case or housing are shaped to keep the filament 58 and the spool 54 clear of sticky clots and clogs.

As is known, when a drainage tube, particularly a chest drainage tube, is typically in place, it is often positioned in such a way as to have one or more slight (and sometimes heavy) bends in the tube. Since the cleaner assembly 28 has to negotiate the length of the drainage tube 22, it must be configured to push around those curves without hanging up or buckling. Moreover, the drainage tube 22, itself, must be kink-resistant and sufficiently stiff so as to maintain an open drainage lumen 34 on the inside of the drainage tube.

Operation of the drainage device 20 to drain fluids in one exemplary application, i.e., draining fluids from the chest of a patient, will now be described. As will be appreciated, those fluids contain blood, blood clots, other biological fluids, materials and debris. Thus, after the distal end of the drainage tube 20 is inserted into the chest of the patient, with the squeegee unit of the cleaner assembly 28 in the retracted or resting position within the drainage lumen 34 proximally of the pressure relief assembly 26 and distally of the array of apertures 30, the suction-operated canister can be turned on whereupon the biological fluid from the patient will be drawn into the drainage lumen and carried to the fluid collection canister as described earlier.

Should it be necessary the clear the contents of the drainage tube of any biological material, e.g., blood clots, etc., adhering to the inner surface of the drainage tube's lumen 34, all that is necessary is for a user to rotate the crank 66 by turning its handle in one rotational direction, e.g., clockwise. This action causes the filament portion 86 to be wound up within the annular recess 90 of the spool, while the filament portion 88 unwinds from within the annular recess 92. The winding upon of the filament portion 86 on the spool pulls that filament portion and the squeegee unit which is fixedly secured to it by the loops 80 and 82 in the proximal direction, whereupon the periphery of the squeegee disk scrapes any adhering biological material off of the inner surface of the drainage lumen. Moreover, the movement of the squeegee unit in the proximal direction carries the biological fluid into the inlet conduit 42 from whence it flows through the case or housing 24 out of the outlet port 44 into the fluid collection canister. During the proximally directed movement of the squeegee unit, the pressure relief assembly 26 operates as described above to equalize the pressure within the drainage lumen and thereby prevent any injury to the patient. After the drainage tube has been sufficiently cleaned of adhering biological material, the squeegee unit can then be moved back to its normal or resting position. To that end, all that is required is for the user to rotate the crank 66 by turning its handle in the opposite rotational direction, e.g., counter-clockwise. This action will cause the filament portion 88 to be wound up within the annular recess 92 of the spool, while the filament portion 86 unwinds from within the annular recess 90. The winding up of the filament portion 88 on the spool pulls that filament portion around the pulley 62, whereupon the filament portion 86 moves in the distal direction carrying the squeegee unit with it in that direction until the squeegee unit is back in its normal or resting position. In that position the drainage device can again operate to drain biological fluids from the patient.

It should be pointed out that while the drainage tube 22 had been discussed in the context of a chest drainage tube, the subject invention contemplates that the drainage device may include drainage tubes particularly configured to drain any types of biological fluids from various other portions of the body of a patient. Thus, various changes can be made to the subject invention to meet the particular needs for the portion of the patient's body to be drained and the biological fluid to be drained. Moreover, the drainage device 20 may be made up of different components than those described above. For example, the piston 54 (or backing body) need not be a cylindrical member like that described above and the manner of securement of the squeegee disk 56 to it need not be accomplished by means of a small bead 60. In this regard the piston 54 can be replaced by a backing body of any shape so long as the backing body serves to hold the squeegee disk in a flat configuration as the squeegee unit is moved in the proximal direction to enable the periphery of the squeegee disk to effectively scrape the inner surface of the drainage lumen 34. For example, the piston could be a sphere with a flat side facing the elastomeric disc. Such a shape would reduce the overall profile of the squeegee assembly. This would potentially aid in the transfer of the squeegee unit around curves and through pinch-points in the tube. Moreover, that backing body should be constructed to enable air or fluid which flows around the periphery of the squeegee disk as it bows into the cup-shaped member when the squeegee unit is pulled in the distal direction to flow past the backing body to equalize the pressure distally of the squeegee disk. Further still, the small bead 60 can be replaced with any component or means for securing the squeegee disk to the center proximal side of the piston or other backing body to enable the disk to bow, whereupon air can flow around its periphery as described above. Thus, the combination of the piston or other backing body and the bead or any other squeegee disk attachment means can be replaced by any structure forming a squeegee edge for effective scraping the inner surface of the drainage lumen during proximally directed movement and for forming a pressure relief valve during distally directed movement. Moreover, the duck bill, one way check valve 104 can be replaced by any suitable check valve and its cracking (operating) pressure can be chosen for the particular medical application.

Without further elaboration the foregoing will so fully illustrate our invention that others may by applying current or future knowledge, adopt the same for use under various conditions of service.

We claim:

1. A drainage device for draining a biological fluid from a body of a patient, said drainage device comprising:
    a) a drainage tube having a sidewall having a drainage lumen extending therethrough, said drainage lumen has an inner surface, said sidewall including a length, a distal end, a distal end portion located adjacent said distal end and proximally thereof, a proximal end portion, and a longitudinal axis extending said length of said sidewall, said proximal end portion being configured for location outside the body of the patient for coupling to a fluid collection canister, said distal end portion of said drainage tube being configured to be introduced into the body of the patient and including an array of plural apertures in communication with said drainage lumen and configured for receipt of a biological fluid from the body of the patient, said drainage tube additionally comprising a pressure relief lumen extending along said sidewall from a point at said proximal end portion to a pressure relief port located distally of said array of apertures;
    b) a pressure relief assembly including a one-way pressure relief valve in communication with said pressure relief port and located within said drainage lumen distally of said array of apertures; and
    c) a lumen cleaner assembly including a squeegee unit located in said drainage lumen proximally of said one-way pressure relief assembly and distally of said array of apertures, said squeegee unit being moveable relative to said drainage lumen by a filament located within said drainage lumen, whereupon pulling of a portion of said filament causes said squeegee unit to move in a proximal direction down said drainage lumen to scrape any biological material off said inner surface of said drainage lumen and to carry any biological material scraped off of said inner surface of said drainage lumen to a passageway coupled to said fluid collection canister for collecting said biological material.

2. The drainage device of claim 1 wherein said one-way pressure relief valve is configured to open during the movement of said squeegee unit in said proximal direction in the event that pressure within said drainage tube distally of said squeegee unit exceeds a predetermined value, whereupon air or fluid is enabled to flow from said pressure relief lumen into and through said one-way pressure relief valve into said drainage lumen distally of said squeegee unit.

3. The drainage device of claim 1 wherein said squeegee unit is configured to be moved in a distal direction through said drainage lumen by pulling on a portion of said filament.

4. The drainage device of claim 2 wherein said squeegee unit is configured to act as a pressure relief valve when it is moved in a distal direction through said drainage lumen, whereupon air or fluid may flow around said squeegee unit from a proximal side of said squeegee unit to a distal side of said squeegee unit.

5. The drainage device of claim 4 wherein said squeegee unit comprises an elastomeric disc having a small central portion fixedly secured to a distally located backing body, said backing body being configured to hold said elastomeric disk in a generally planar state when said squeegee unit is moved in said proximal direction and enable said elastomeric disk to bend or bow into a generally cup-shaped member when said squeegee unit is moved in said distal direction.

6. The drainage device of claim 5 wherein said backing body comprises a cylindrical piston having plural longitudinal passageways extending therethrough and a generally planar proximal surface abutting said elastomeric disk.

7. The drainage device of claim 1 additionally comprising a housing having a hollow interior, a first port in fluid communication with said hollow interior, a second port in fluid communication with said hollow interior, and a third port in fluid communication with said hollow interior.

8. The drainage device of claim 7 wherein said first port is configured to be connected to said proximal end portion of said drainage tube, and wherein said second port is configured to be connected to a conduit coupled to the fluid collecting canister.

9. The drainage device of claim 8 wherein lumen cleaner assembly comprises a pulley located in said distal end portion of said sidewall and about which said filament extends, and wherein one portion of said filament is fixedly secured to said squeegee unit.

10. The drainage device of claim 9 wherein said lumen cleaner assembly additionally comprises a rotatable spool located in said housing, said spool being configured to have portions of said filament wrapped around said spool, said spool being rotatable in one direction to cause said filament to move said squeegee unit through said drainage lumen in a distal direction and also being rotatable in a second direction, opposite to said first direction, to cause said filament to move said squeegee unit through said drainage lumen in said proximal direction.

11. A method of draining a biological fluid from a body of a patient, said method comprising:
a) providing a drainage device comprising a drainage tube having a sidewall with a drainage lumen extending therethrough, said drainage lumen having an inner surface, said sidewall including a length, a distal end, a distal end portion located adjacent said distal end and proximally thereof, a proximal end portion, and a longitudinal axis extending said length of said sidewall, said proximal end portion being configured for location outside the body of the patient for coupling to a collection canister located outside the body of the patient, said distal end portion of said drainage tube including an array of plural apertures in said sidewall in communication with said drainage lumen and configured for receipt of said biological fluid from the body of the patient, said drainage tube also comprising a pressure relief lumen extending along said sidewall from a point at said proximal end portion to a pressure relief port located distally of said array of apertures;
b) providing a pressure relief assembly within said drainage lumen distally of said array of apertures and including a one-way pressure relief valve in communication with said pressure relief port;
c) providing a lumen cleaner assembly including a squeegee unit in said drainage lumen proximally of said one-way pressure relief assembly and distally of said array of plural apertures, said squeegee unit being moveable relative to said drainage lumen by a filament located within said drainage passageway;
d) introducing said distal end portion of said drainage tube into the body of the patient whereupon biological fluid the said body of the patient flows into said plural apertures and from there through said drainage tube for collection in said collecting canister; and
e) scraping biological material adhering to said inner surface of said drainage lumen off of said inner surface of said drainage lumen by pulling a portion of said filament to cause said squeegee unit to move in a proximal direction down said drainage lumen to scrape such biological material off said inner surface of said drainage lumen and to carry any such biological material scraped off of said inner surface of said lumen to a passageway coupled to said collection canister for collecting said biological material.

12. The method of claim 11 wherein said one-way pressure relief valve is configured to open during the movement of said squeegee unit in said proximal direction in the event that pressure within said drainage tube distally of said squeegee unit exceeds a predetermined value, whereupon air or fluid is enabled to flow from said pressure relief lumen into and through said one-way pressure relief valve into said drainage lumen distally of said squeegee unit.

13. The method of claim 11 additionally comprising pulling a portion of said filament to cause said squeegee unit to move in a distal direction through said drainage lumen, whereupon said squeegee unit is brought back to a position distally of said array of apertures.

14. The method of claim 13 wherein said squeegee unit is configured to act as a pressure relief valve when it is moved in said distal direction through said drainage lumen, whereupon air or fluid may flow around said squeegee unit from a proximal side of said squeegee unit to a distal side of said squeegee unit.

* * * * *